US010456101B2

(12) United States Patent
Wang et al.

(10) Patent No.: US 10,456,101 B2
(45) Date of Patent: Oct. 29, 2019

(54) BREAST TOMOSYNTHESIS WITH FLEXIBLE COMPRESSION PADDLE

(71) Applicant: General Electric Company, Schenectady, NY (US)

(72) Inventors: Xin Wang, Clifton Park, NY (US); Bernhard Erich Hermann Claus, Niskayuna, NY (US); Cynthia Elizabeth Landberg Davis, Niskayuna, NY (US); Razvan Gabriel Iordache, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 15/935,879

(22) Filed: Mar. 26, 2018

(65) Prior Publication Data

US 2018/0214106 A1    Aug. 2, 2018

Related U.S. Application Data

(63) Continuation of application No. 15/062,838, filed on Mar. 7, 2016, now Pat. No. 9,943,280.

(51) Int. Cl.
*A61B 6/04* (2006.01)
*A61B 6/00* (2006.01)
*A61B 8/08* (2006.01)
*A61B 6/02* (2006.01)
*G06F 19/00* (2018.01)
(Continued)

(52) U.S. Cl.
CPC .............. *A61B 6/502* (2013.01); *A61B 6/025* (2013.01); *A61B 6/0414* (2013.01); *A61B 6/4417* (2013.01); *A61B 6/461* (2013.01); *A61B 6/5217* (2013.01); *A61B 6/5258* (2013.01); *A61B 8/0825* (2013.01); *G06F 19/00* (2013.01); *G16H 50/50* (2018.01); *A61B 5/1075* (2013.01); *A61B 6/5205* (2013.01); *A61B 2090/3908* (2016.02); *A61B 2090/3937* (2016.02); *A61B 2090/3966* (2016.02); *G06T 11/003* (2013.01);
(Continued)

(58) Field of Classification Search
CPC .... A61B 2090/3908; A61B 2090/3937; A61B 2090/3966; A61B 6/025; A61B 6/0414; A61B 6/4417; A61B 6/461; A61B 6/502; A61B 6/5258
See application file for complete search history.

(56) References Cited

U.S. PATENT DOCUMENTS

| | | | | |
|---|---|---|---|---|
| 9,943,280 B2 * | 4/2018 | Wang | ................... | A61B 6/5258 |
| 2008/0181360 A1 * | 7/2008 | Hemmendorff | ........ | A61B 6/502 378/37 |
| 2014/0226786 A1 * | 8/2014 | Goossen | .............. | A61B 6/0414 378/37 |

* cited by examiner

*Primary Examiner* — Mark R Gaworecki
(74) *Attorney, Agent, or Firm* — Fletcher Yoder, P.C.

(57) ABSTRACT

A method of breast image reconstruction includes positioning a breast on an imaging system support plate, compressing the breast with a flexible paddle, obtaining imaging data, estimating a breast thickness profile by at least one of placing markers on the breast, performing an image-based analysis of the obtained data, using an auxiliary system, and performing a model-based computation. The three-dimensional (3D) reconstruction including using a thickness profile of the breast surface in at least one of an iterative reconstruction, a filtered back-projection reconstruction, and a joint reconstruction performed using information obtained from an ultrasound scan. A non-transitory medium having executable instructions to cause a processor to perform the method is also disclosed.

30 Claims, 9 Drawing Sheets

(51) Int. Cl.
*G16H 50/50* (2018.01)
*A61B 90/00* (2016.01)
*A61B 5/107* (2006.01)
*G06T 11/00* (2006.01)

(52) U.S. Cl.
CPC .............. *G06T 2207/10112* (2013.01); *G06T 2207/30004* (2013.01); *G06T 2207/30068* (2013.01)

T = HEIGHT AT REFERENCE POINT
H = T + PADDLE_HEIGHT/2

BREAST TOMOSYNTHESIS WITH FLEXIBLE COMPRESSION PADDLE

CROSS-REFERENCE TO RELATED APPLICATIONS

This application is a continuation of U.S. patent application Ser. No. 15/062,838, filed on Mar. 7, 2016 the disclosure of which is incorporated herein by reference in its entirety.

BACKGROUND AND SUMMARY

In modern healthcare facilities, non-invasive imaging approaches are used for identifying, diagnosing, and treating diseases. One purpose to which such techniques are applied is the acquisition of images of the breast for use in identifying and diagnosing lesions or irregularities in the breast tissue.

In conventional mammography approaches, breast imaging may be implemented using radiographic techniques, such as by projecting X-rays through the breast tissue and reconstructing images based on the differential transmission of the X-rays through the tissue. Such approaches, however, may suffer from various detriments. For example, conventional radiographic imaging techniques are generally planar or two-dimensional (2D) in nature, limiting the ability of a diagnostician to visualize the results.

An alternative approach to conventional radiographic mammography involves an imaging technique known as tomosynthesis. In tomosynthesis X-ray attenuation data is obtained for a region of interest over an angular range (e.g., about typically 15 to 60 degrees) and this data is used to construct volumetric or generally three-dimensional (3D) reconstructions of the breast tissue. In general, tomosynthesis imaging exhibits good in-plane resolution with, potentially, poorer depth resolution. In this manner, tomosynthesis may be employed to non-invasively detect abnormalities in the breast tissue, such as lumps, fibroids, lesions, calcifications, and so forth. Such tomosynthesis systems are generally effective for detailed characterization of benign and cancerous structures such as calcifications and masses embedded in the breast tissue.

Another imaging approach for use in imaging breast tissue is ultrasound. An ultrasound imaging system uses an ultrasound probe for transmitting ultrasound signals into an object, such as the breast of the patient being imaged, and for receiving reflected ultrasound signals there from. The reflected ultrasound signals received by the ultrasound probe are generally indicative of boundary transitions between structures in the imaged region and may be used to reconstruct an image of the interior of the imaged anatomy. In general, ultrasound may exhibit good depth-resolution combined with a somewhat reduced in-plane resolution. Ultrasound imaging is useful as an alternate tool for diagnosis, such as for differentiating benign cysts and masses. In addition, ultrasound imaging may be used as a secondary screening tool in women with breasts that are dense. In dense breast tissue X-ray imaging is not as sensitive and the addition of ultrasound imaging has been shown to find more cancers.

A mammography system can have a compression plate to compress the breast against the image receptor which holds an X-ray detector. The mammography system can also contain an anti-scatter grid. The main purpose of the breast compression is to spread the tissue out and hold the tissue in place. For a tomosynthesis examination, the breast is positioned and compressed in the same way as for a mammogram but the X-ray tube moves in an arc around the breast and multiple X-ray images at different angles are taken. The information from the detector is sent to a computer, which produces a three-dimensional (3D) image of the breast. The X-ray dose for an individual tomosynthesis image is less than a regular mammogram, but the total dose for the examination is similar to that of a two-dimensional (2D) mammography examination. Using a flexible paddle for breast compression during mammography and tomosynthesis gives the patient the benefit of less pain and more comfort, and enables a potential for integration with breast ultrasound imaging. One of the big challenges however is that the top surface of the breast is not flat (e.g., angled, and/or non-planar) as when using a flat rigid paddle. This surface shape of the compressed breast has an impact on both the breast density estimation and the reconstruction of the 3D image.

DETAILED DESCRIPTION

Embodying systems and methods extract the compressed breast thickness profile and apply it to improve the breast density estimation and breast image reconstruction when data is obtained using a flexible compression paddle. In accordance with embodiments, the breast surface geometry (i.e., the breast thickness profile when the breast is compressed with the flexible paddle) is captured using markers or auxiliary devices, or using a completely image based method, or a model-based method, or a combination of several of them. The breast thickness profile is applied in breast density estimation to improve accuracy; in data pre-processing and image reconstruction to improve image quality; and in image display to improve the readability and interpretation of the image by the radiologist.

Figure 1:
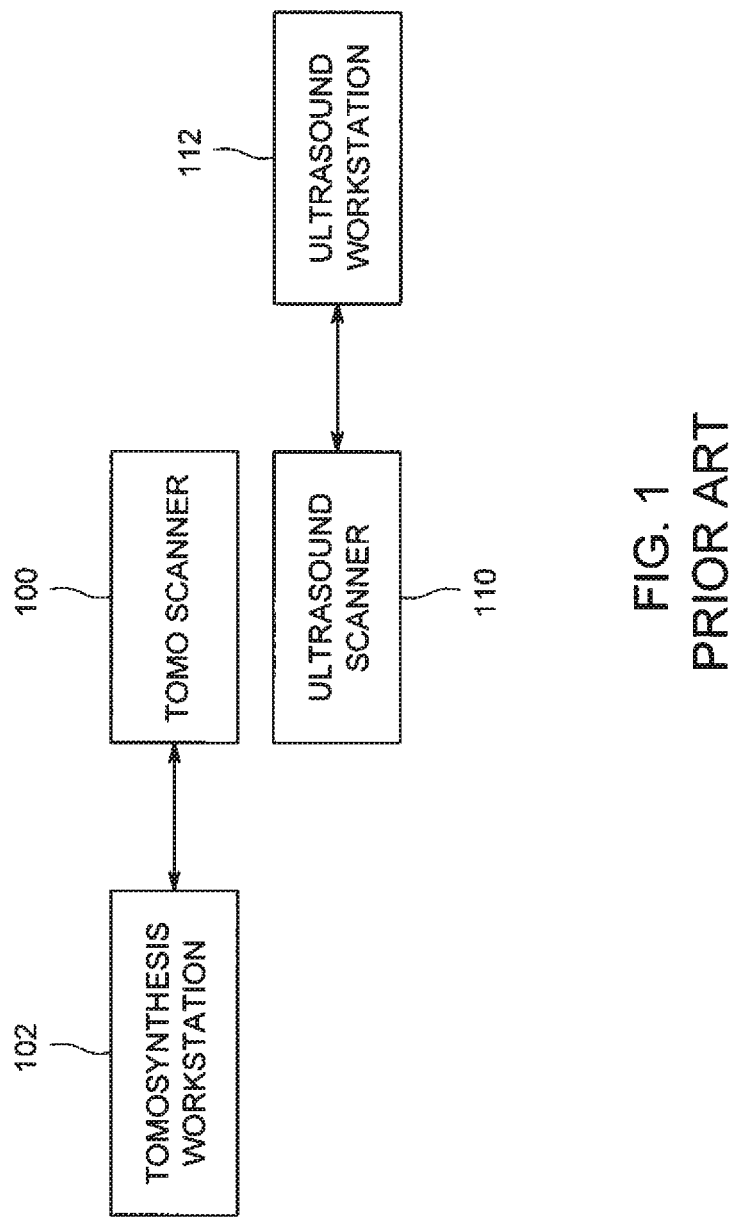
FIG. 1 depicts conventional sequential separate tomosynthesis and ultrasound imaging.

FIG. 1 depicts conventional tomosynthesis and ultrasound breast scan systems. In this example, a tomosynthesis scanner 100 is provided in conjunction with a tomosynthesis workstation 102 that controls operation of the scanner 100. For example, a user may configure or initiate a tomosynthesis scan using the scanner 100 via the workstation 102 or may review tomosynthesis images generated during a scan session using the scanner 100.

In the depicted example, the tomosynthesis scanner 100 is provided in proximity to an ultrasound scanner 110, which may have a probe or other scan components which can be used to ultrasonically scan the patient during the same session, such as before or after the tomosynthesis acquisition. For example, the ultrasound image acquisition may be performed immediately after the tomosynthesis image acquisition, while the patient is still in the same position and under compression. As with the tomosynthesis scanner 100, the ultrasound scan components 110 are shown as being in communication with an ultrasound workstation 112, which may be used to configure or program an ultrasound acquisition using the scanner 110 or to view the results of such a scan.

Alternatively, the ultrasound scanner electronics and control may be performed by the tomosynthesis system as well. In some implementations, the different elements of an ultrasound system and a tomosynthesis system may be fully integrated, combined, partially integrated, or stand-alone for each. For workflow reasons it would be of particular interest to combine at least the operator interface and display modules. The ultrasound system can also include a system controller/motion controller to control the movement (e.g., sweep) of the ultrasound probe.

Ultrasound workstation 112 is in communication with the ultrasound scanner 110. The ultrasound probe of the scanner 110 can be moved automatically to perform an ultrasound acquisition. A user may configure the scan via the workstation 112 and, based upon the configured scan, the ultrasound scan components are moved so as to acquire ultrasound images corresponding to the requested scan. The ultrasound probe can have several motion paths, which may also be specific to the characteristics of the particular ultrasound probe that is being used. For example, for an elongated probe a motion in a single sweep starting at, and away from the patient's chest wall, may be sufficient to provide full coverage the imaged breast; alternatively, a standard probe may require a raster scan (or similar path) for sufficient anatomical coverage; additionally, other scan paths are possible.

Figure 2:
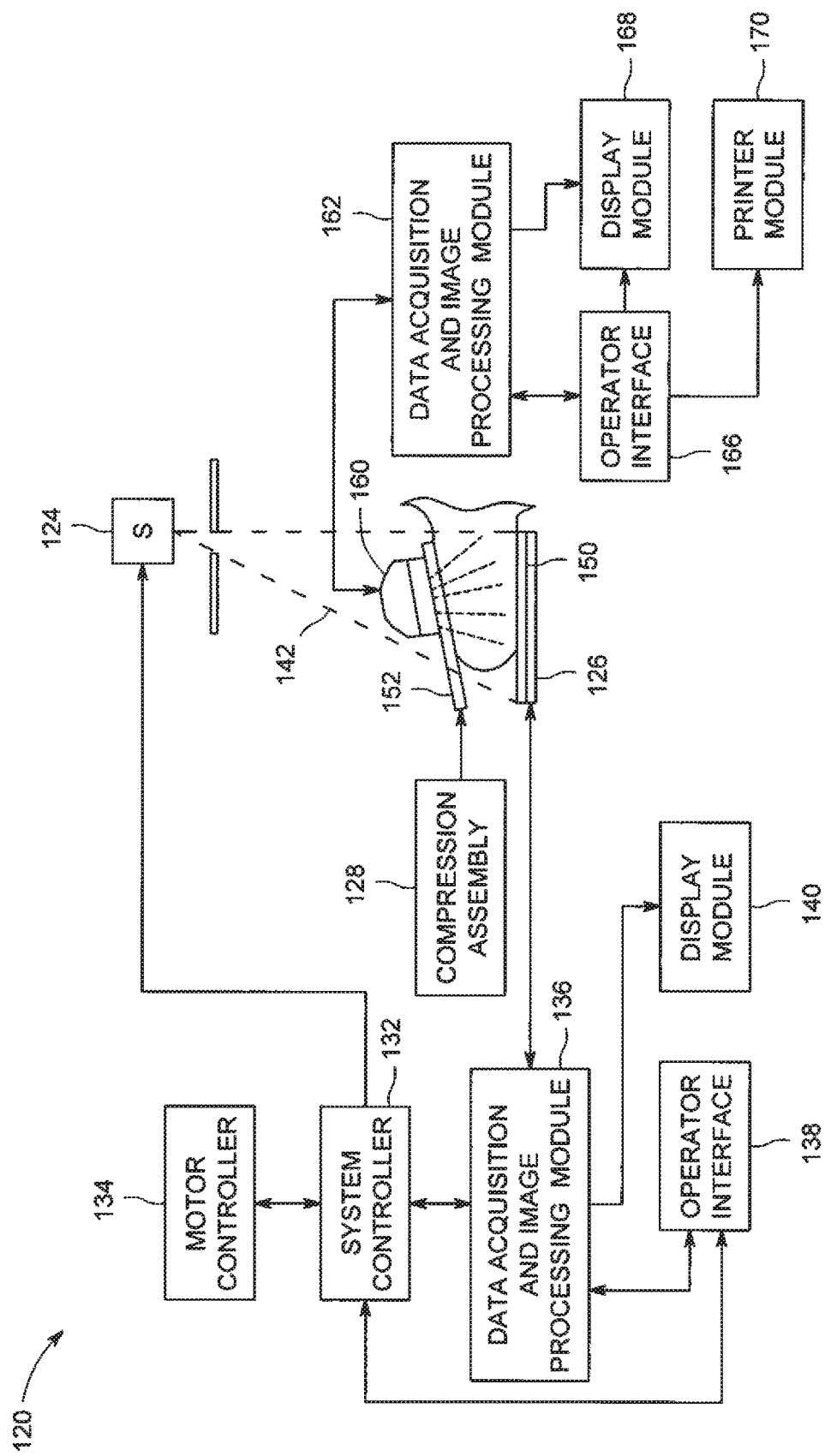
FIG. 2 depicts a multi-modality mammography imaging system.

FIG. 2 depicts a combined, multi-modality mammography imaging system 120 (including both tomosynthesis and ultrasound components). As depicted, the imaging system 120 includes a tomosynthesis image data acquisition subsystem for acquiring tomographic image data. The tomosynthesis imaging subsystem includes an X-ray source 124, an X-ray detector 126 and a compression assembly 128 that may be used to position the patient tissue and to generate signals representative of X-ray transmission through the tissue of interest. The tomosynthesis imaging subsystem further includes a system controller 132 (e.g., a central processor or control processor), a motor controller 134, data acquisition and image-processing module 136, an operator interface 138 and a display module 140, some or all of which may be embodied as the tomosynthesis workstation 102.

The X-ray source 124 may, in certain implementations, include an X-ray tube (or other suitable X-ray generating mechanism) and a collimator configured to generate a beam of X-rays 142 when active. In an implementation of a tomosynthesis imaging system, the X-ray source 124 is movable in a one, two or three-dimensional (3D) trajectory relative to the volume being imaged (such as along a line or a curve) such that the X-ray source moves over a limited angular range relative to the volume being imaged. Movement of the X-ray source may be manual, automated, or some combination (e.g., manual initial positioning with automated movement during scanning).

An X-ray filtration slot on the outside of the X-ray tube assembly may be provided. When the flexible compression paddle is used added filtration can be added to absorb the low energy X-rays normally absorbed by the plastic compression paddle. These X-rays do not penetrate the breast and only serve as added skin dose. Alternatively, this added filtration can be automatically inserted and internal to the X-ray tube system for when the mesh paddle is inserted.

The X-ray detector 126 may be stationary, or may be configured to move either independently or in synchrony with the X-ray source 124. In a mammography embodiment, the X-ray detector 126 may be positioned proximate to and beneath the breast tissue of the patient, and thus may be incorporated as part of or proximate to the compression assembly 128. For example, the X-ray detector 126 may be disposed immediately or proximately beneath a bottom plate of compression assembly 128 such that the breast tissue does not rest directly on the detector 126 but on a plate or other compression support above the detector 126. In one embodiment, the breast can rest directly on the detector cover plate (i.e., the detector cover plate comprises the bottom plate of the compression assembly). In addition, an anti-scatter grid may be placed between the detector and the compression support. This anti-scatter grid may be stationary or may move during image acquisition in order to reduce the effects of the form (lines) of the grid from appearing in the image.

In certain breast imaging embodiments, the compression assembly 128 is configured to compress the breast tissue during both tomosynthesis and ultrasound image acquisitions. In particular, the compression assembly 128 may be used to stabilize the imaged breast tissue during acquisition of both the tomosynthesis and the ultrasound datasets and to generally maintain uniformity (position and thickness) of the tissue both during and between image acquisitions. Thus, in practice, at least part of the compression structures of the assembly 128 may transmit X-rays (i.e., may be radiolucent) for the tomosynthesis image acquisition; and may transmit the ultrasound signals (i.e., may be sonolucent) for the ultrasound image acquisition. In one embodiment, the compression assembly includes a bottom plate 150, (such as a flat, inflexible plate) on which the breast tissue may rest, and an upper plate or paddle 152 which lowers onto the breast tissue to effect compression. In one implementation, the upper paddle 152 is non-rigid across at least a portion of its surface. For example, the upper paddle 152 may be formed using a flexible thin layer of material, e.g., a film-like or mesh material (i.e., formed as a mesh paddle) that is both radiolucent and sonolucent and which is at least partially conformable to the shape and size of the breast tissue. The bottom paddle is generally only radiolucent. But, may be made sonolucent in the case of ultrasound imaging from the top and bottom of the breast. In accordance with embodiments, a hybrid compression paddle may be used that is rigid across all of its surface with a mesh layer in contact with the skin. The rigid portion may be removed for ultrasound scanning leaving only the mesh component in contact with the skin.

In a tomosynthesis implementation, and unlike conventional radiographic mammography techniques, it is less critical for the breast tissue to be compressed to a substantially uniform thickness or to significantly reduce thickness. Furthermore, as the tissue structures that overlap in 2D imaging can be resolved with tomosynthesis the breast tissue does not require compression in order to spread out the tissue. That is, due to the nature of the tomosynthesis image acquisition process, the breast tissue need not be thin and of uniform thickness in order to generate useful diagnostic images. Likewise, the ultrasound image acquisition does not require that the breast tissue be of uniform thickness. Thus, in certain embodiments the upper plate 152 may rotatably conform to the compressed breast or approach the lower plate 150 at an angle such that, when engaged, the paddles or plates 150, 152 are not essentially parallel to one another but, instead, remain at an angle with respect to one another. Such accommodative compression may reduce patient discomfort by at least partly conforming to the shape of the breast tissue. In addition, the flexible paddle may, to some extent, conform to the shape of the breast.

Figure 5A:
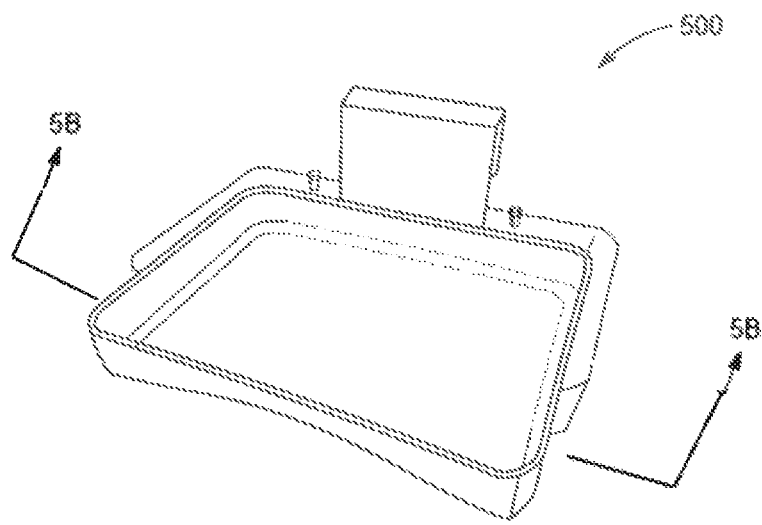
FIG. 5A depicts a flexible paddle in accordance with embodiments.
Figure 5B:
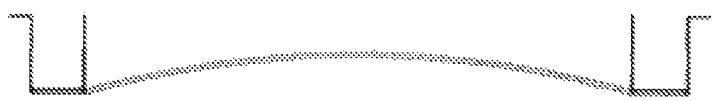
FIG. 5B depicts a cross-sectional view of the flexible paddle of FIG. 5A along line 5B-5B in accordance with embodiments.

FIG. 5A depicts flexible paddle 500 in accordance with some embodiments. FIG. 5B depicts a cross-sectional view of paddle 500 along lines 5B-5B. In some embodiments, the flexible paddle may be sufficiently taut such that it retains its shape even when the breast is under compression. The flexible paddle may be constructed such that it is essentially a film or mesh that is held by a frame which may have curved sides, e.g., to increase patient comfort. The mesh/film may then conform to the shape of the frame and (under compression) to the shape of the compressed breast, resulting in an imaged volume bounded by a curved top layer (defined by the compression paddle). In embodiments where an ultrasound scan is performed, the shape of the compression paddle (and, potentially, its frame), and the shape of the ultrasound probe may be matched. In some implementations, embodiments are not so limited and can also apply to rigid compression paddles (which may be non-planar and/or positioned at an angle that is not parallel to the detector cover).

Figure 3:
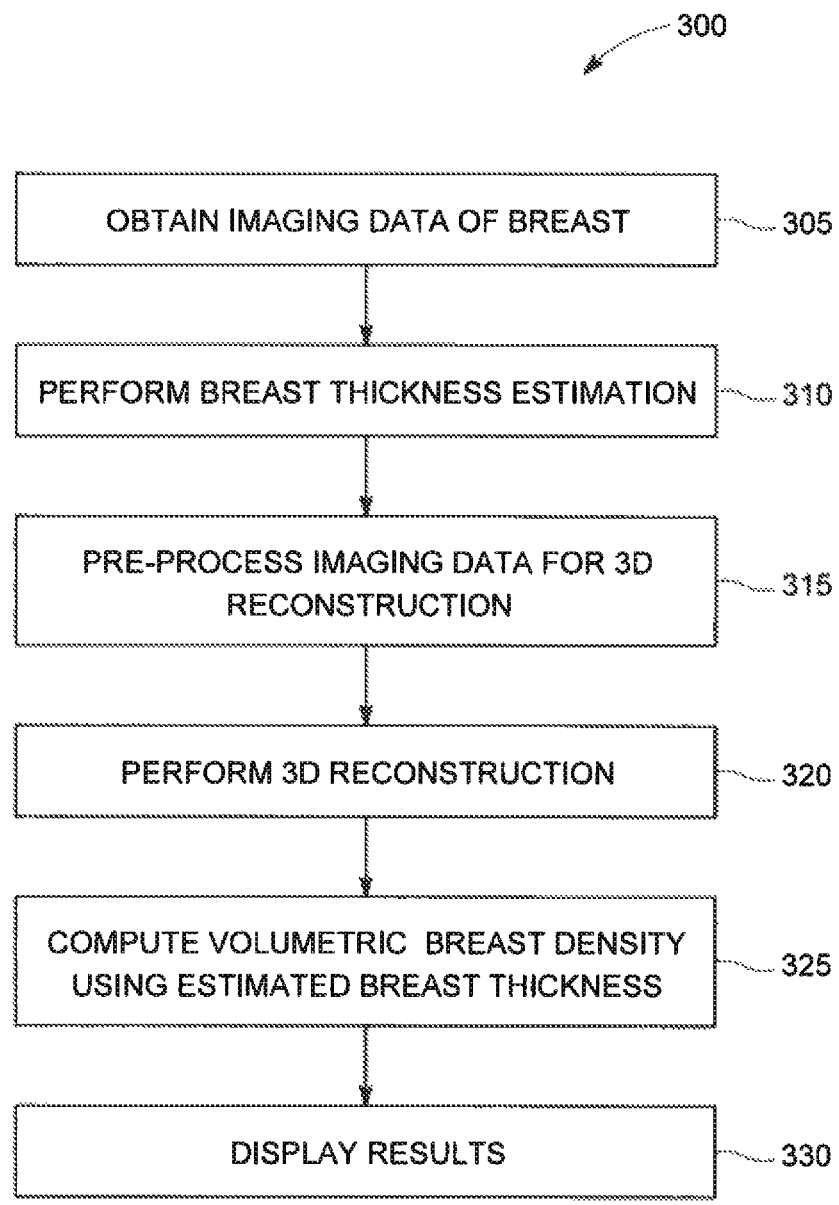
FIG. 3 depicts a process for breast image reconstruction in accordance with embodiments.

In the depicted implementation of FIG. 3, the system controller 132 controls operation of the tomosynthesis imaging subsystem and provides for any physical motion of the X-ray source 124 and/or the X-ray detector 126. In the depicted embodiment, mechanical movement of the imaging components is affected via the motor controller 134 in accordance with a prescribed imaging trajectory for use in tomosynthesis. Therefore, by means of the tomosynthesis imaging subsystem, the system controller 132 may facilitate acquisition of radiographic projections at various view angles along a limited angular range relative to a patient. In general, the system controller 132 commands operation of the tomosynthesis imaging system 120 to execute examination protocols and to acquire resulting data.

In one implementation, the tomosynthesis data acquisition and image-processing module 136 communicates with the X-ray detector 126 and typically receives data from the X-ray detector 126, such as a plurality of sampled analog signals or digitized signals resulting from exposure of the X-ray detector to X-rays. The tomosynthesis data acquisition and image-processing module 136 may convert the data to digital signals/images (e.g., projection images) suitable for processing and/or may process sampled digital and/or analog signals/images to generate volumetric images of the breast tissue which may, in turn, be displayed on the display module 140.

The operator interface 138 can be used to customize settings for the tomosynthesis imaging and for effecting system level configuration changes as well as for allowing operator activation and operation of the tomosynthesis imaging system 120. In the depicted embodiment, the operator interface 138 is connected to the system controller 132, image-processing module 136, and the display module 140.

Shown in conjunction with the tomosynthesis imaging subsystem components discussed above are ultrasound imaging system components that may be present in a combined (i.e., multi-modality) system. In the depicted example, the ultrasound imaging subsystem includes an ultrasound probe 160, an ultrasound data acquisition and image-processing module 162, which includes beam-formers and image reconstruction and processing circuitry, an operator interface 166, a display module 168 and a printer module 170. In a multi-modality imaging system based upon both X-ray and ultrasound techniques, certain of these components or modules may be partially or fully integrated to perform image acquisition and processing for both systems. Alternatively, in other implementations, both the X-ray and ultrasound subsystems may be largely autonomous from one another, with separate user workstations or interfaces as well as separate scan subsystems.

In certain embodiments, the ultrasound imaging subsystem uses the ultrasound probe 160 for transmitting a plurality of ultrasound signals into an object, such as the breast tissue of a patient being imaged, and for receiving a plurality of reflected ultrasound signals from the tissue. In certain implementations, the ultrasound imaging subsystem may employ beam steering techniques to help image all areas of the breast tissue. The reflected ultrasound signals from the tissue convey information about thickness, size, and location of various tissues, organs, tumors, and anatomical structures in relation to transmitted ultrasound signals. The plurality of reflected ultrasound signals received by the ultrasound probe 160 are processed for constructing a volumetric image of the object.

In certain embodiments, movement and operation of the ultrasound probe 160 is automated. In these embodiments, the ultrasound probe 160 may be automatically brought into contact with the tissue being imaged or with the overlying sonolucent paddle structure 152 compressing the breast tissue. The ultrasound probe 160 may then be moved via a mechanical subsystem (e.g., motion controller/automation module 114 of FIG. 1, which may be provided as a component of the data acquisition module 162) to move with respect to the breast tissue while acquiring ultrasound image data. In some embodiments, upon completion of the prescribed acquisition protocol, one or both of the ultrasound probe 160 or the underlying paddle 152 may be automatically disengaged from the tissue. In certain implementations, the ultrasound probe 160, and any radiopaque supporting structures, are removed from the X-ray beam path when a tomosynthesis examination is being performed or, more generally, when an ultrasound examination is not being performed.

The ultrasound data acquisition and image-processing module 162 sends signals to and receives information from the ultrasound probe 160 during an imaging procedure. Thus, the ultrasound data acquisition and image-processing module 162 may control the strength, beam focus or forming, duration, phase, and frequency of the ultrasound signals transmitted by the ultrasound probe 160, and may decode the information contained in the plurality of reflected ultrasound signals from the tissue to a plurality of discernable electrical and electronic signals. Once the information is obtained, an ultrasound image of the object located within a region of interest is reconstructed in accordance with generally known reconstruction techniques.

The operator interface 166 may include a keyboard, a mouse, and other user interaction devices. The operator interface 166 can be used to customize a plurality of settings for an ultrasound examination (including settings related to the automated operation of the probe 160), to effect system level configuration changes, and to allow operator activation and operation of the ultrasound imaging system 32. The operator interface 166 is connected to the ultrasound data acquisition and image-processing module 162, the display module 168 and to the printer module 170, some or all of which may be provided as the ultrasound workstation 112 of FIG. 1. The display module 168 receives image information from the ultrasound data acquisition and image-processing module 162 and presents the image of the object within the region of interest of the ultrasound probe 160. The printer module 170 is used to produce a hard copy of the ultrasound image in either gray-scale or color. As noted above, some or all of these system components may be integrated with those of the tomosynthesis X-ray system described above. Display of images/data, etc. may be appropriately coordinated between modalities. For example, corresponding locations/cross-sections through both volumes (tomosynthesis and ultrasound) may be displayed side-by-side, or overlaid, to provide ease of workflow/interpretation to the radiologist.

FIG. 3 depicts process 300 for breast image reconstruction in accordance with embodiments. Process 300 mitigates artifacts in the reconstructed volumetric image (e.g., out-of-lane artifacts) that are due to the use of a flexible/deformable (and in particular non-planar) compression paddle during the imaging scan(s). Image data of the breast is obtained, step 305, where the breast is compressed using a flexible paddle. The breast thickness (and in particular a thickness profile of the breast—a representation of the spatially varying thickness of the compressed breast) is estimated, step 310. In one implementation, the estimation can be performed either by using markers placed on the breast and/or the compression paddle, and/or by using anatomical markers (e.g., using skin texture, Cooper's ligaments, etc.). In another implementation the breast thickness can be completely image intensity based. In yet another implementation, the breast thickness can be obtained by a model based approach, and/or other auxiliary devices. In accordance with embodiments, a hybrid approach of breast estimation can combine, for example, marker-based and image intensity based techniques.

Prior to 3D reconstruction, the imaging data is pre-processed, step 315. Before reconstruction one or more correction steps may be performed on the projection images. These correction steps may be purely image based methods, or they may comprise steps based on the estimated or measured thickness profile of the breast. These pre-processing steps may include an image-based shading correction that performs a thickness compensation-type processing where gray scale values in the image are modified such that the resulting image looks like the breast is of uniform constant thickness, where the "added thickness" is determined as possibly being a uniform "fatty" or similar material. Gray scale values corresponding to the "added thickness" are smoothly varying in the interior of the breast region (thereby reflecting the smoothly varying breast thickness profile) and compensating the image to reflect a "constant thickness" up to and including the skin line. In one embodiment, this thickness compensation may extend into the "air" region of the projection images. That is, in image regions where the rays from the X-ray source to the pixel pass only through air (and possible compression paddle) and not through breast tissue, the pixels are modified such as to represent a constant thickness of fat (or other uniform material). Processing steps may also be performed to ensure consistency between views corresponding to different view angles (i.e., in each view the breast is corrected to the same effective thickness, the "added thickness" for different views is consistent, etc.). The pre-processing steps may also include a step to convert images such that pixel values represent an average attenuation along a path length (instead of a line integral along a path as may be typically used). These two correction approaches can be combined (where the image is filled up with fat to a constant height, and/or the conversion to an average attenuation along the path), along with other appropriate pre-processing steps (that correct, e.g., for other geometry effects and non-uniformities).

At step 320, the 3D reconstruction is performed. The reconstruction can use the breast surface geometry in an iterative reconstruction; the breast surface geometry can be used in back-projection reconstruction; or a joint reconstruction can be performed using information from an ultrasound scan to guide the tomosynthesis reconstruction.

In accordance with embodiments, iterative 3D reconstruction using the breast surface geometry can include building an exact model matching the surface geometry of the breast, where every voxel in the model belongs to the breast. This approach eliminates those voxels that do not belong to the breast in the original rectangular model, and can help with reducing the computation time and improves the ill posed nature of the inverse problem. Accuracy of the forward projection can improve, thus improving accuracy of the inverse solution and accelerating the convergence rate. In addition, by using geometry prior, the total number of unknowns are reduced, and thus the computation time needed will be reduced as a result.

Figure 6:
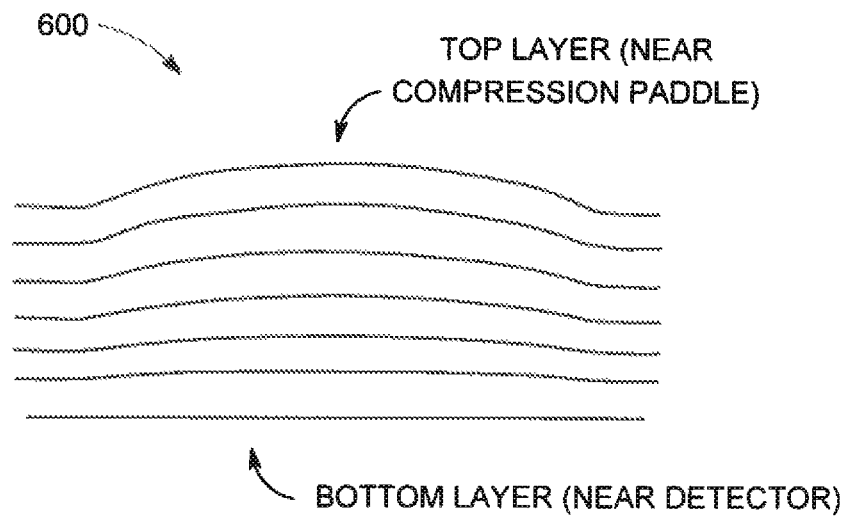
FIG. 6 depicts a discretization of a volumetric image with a non-uniform voxel grid representing a smoothly varying thickness profile in accordance with embodiments.

If using discrete grids, one problem can be an artifact in the forward projection due to the stepped edge of the model (which is a consequence of the voxelization of the smoothly varying thickness profile). FIG. 6 depicts volume 600 with a smoothly varying thickness profile. FIG. 6 illustrates one embodiment utilizing non-uniform voxels (only height of voxels is shown). In one embodiment, the geometry of the non-uniform voxel grid in-plane corresponds to the conventional uniform x/y grid; and for a given x/y location, all voxels have essentially the same thickness. The voxel thickness across the image is varying smoothly such that at any given x/y location N voxels add up to the full thickness as defined by the thickness profile at that location (where N is a fixed number of slices in the reconstructed volume). In another embodiment, when discretizing this volume (which is bounded by the curved thickness profile) with a conventional Cartesian voxel grid, the curved top edge of the model will be represented by a stepped edge due to the discrete voxel size/shape. One approach to solve this problem is to add a buffer layer to the model to make it rectangular, and assign fatty tissue to the buffer layer. During each iteration, the whole volume including the buffer area can be updated, with some smoothing (or other appropriate processing) applied over the buffer area. The smoothing can be stronger in areas that are farther away from the breast surface (and outside of the breast), and less strong closer to the boundary of breast to preserve information at the breast boundary. In accordance with embodiments, constraints can be set—for example, enforcing (as part of an iterative algorithm) uniformity outside of the 3D region that is known to be filled with tissue by appropriate smoothing, or setting to a uniform value while making sure the transition to tissue region is smooth.

In accordance with embodiments, using the breast surface geometry to perform a filtered back-projection based reconstruction, a model matching the surface geometry of the breast in which every voxel belongs (at least partially) to the breast can be constructed. In one embodiment, the model consists of an approximation of the true volume with a Cartesian voxel grid reflecting the curved top surface. By performing a back projection to such a model, a reconstructed breast volume can be obtained. This reconstructed volume can have a clearly defined boundary between breast tissue and air. In other implementations, the back projection can be to a rectangular volume instead of the exact model. The curved breast surface geometry may then be applied to the rectangular volume as a mask to obtain the reconstructed volume of the breast. In one embodiment, the "outside" of the breast (e.g., within a rectangular voxel grid) may be set to a constant value.

Figure 7:
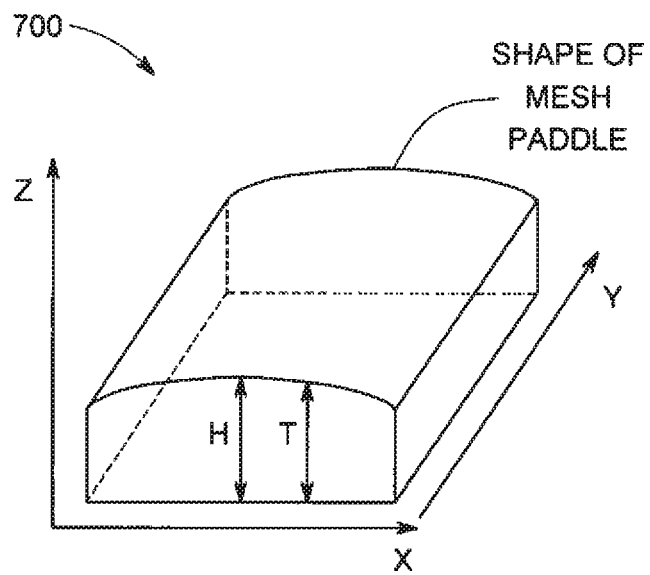
FIG. 7 depicts a geometry of a reconstructed volume in accordance with embodiments.

In another embodiment, the back projection or iterative reconstruction can be into a model with non-uniform voxels. The voxels can be slices of variable dimension (e.g., voxel height and/or thickness); that are variable as a function of voxel location in x- and y-planes, while voxel number is constant at all locations. FIG. 6 illustrates this principle of a variable height/variable thickness (while maintaining the conventional voxel grid in x/y). In one embodiment, the top layer of voxels in such a grid may conform to the curved breast surface; the bottom layer may conform to the bottom plate of the compression assembly, and for a given x/y location the voxel thickness may be constant. In one example, the breast thickness near the center may be about 15% higher than the thickness near the edges. Consequently, the voxels near the center may then be about 15% "thicker" (in z axis) than the voxels near the edges; thereby enabling a representation of the volume with a constant number of slices and without creating any stepping artifacts due to the discrete voxel grid. FIG. 7 depicts the geometry of reconstructed volume 700, where the volume is bounded at the top by a curved surface—(i.e., the non-planar shape of the flexible compression paddle).

After performing the 3D reconstruction (step 320), the results of the reconstruction can be displayed, step 330, with uniform voxels and the exact model of the breast. When using the flexible compression paddle, the top slices (in a fixed Cartesian voxel grid) usually have smaller footprint than the bottom slices. The extent of the top slices, when displayed individually, relative to the patient's chest wall and nipple are unknown. To help with visualization for the display, an indication of the slice corresponding to the largest footprint can be added to all other slices (e.g., as a superimposed contour of the breast in the slice with the largest footprint; or, as the contour of the combined footprints across all slices), and any image areas outside of the breast can be displayed in a uniform gray value.

Figure 8:
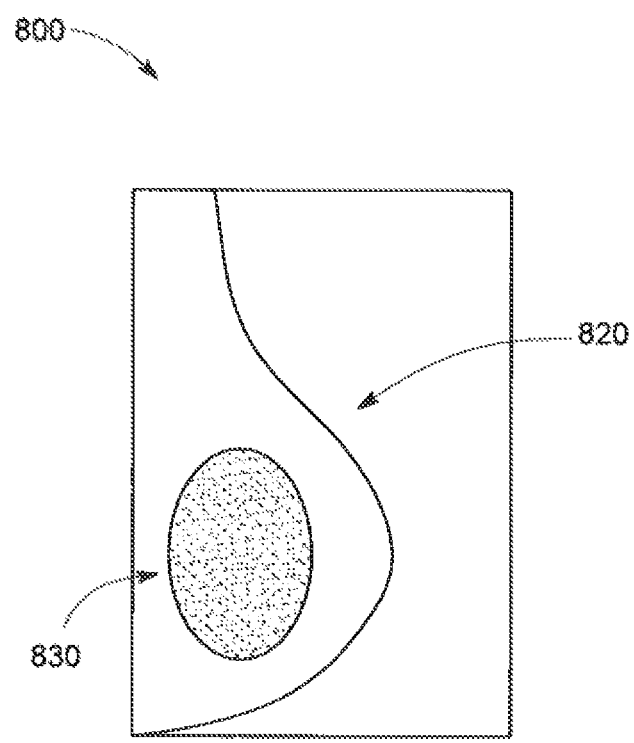
FIG. 8 depicts the display of volumetric image information superimposed with breast shape/contour in accordance with embodiments.

One example of such a display is shown in FIG. 8, which depicts volumetric image information 800 superimposed with breast shape/contour 820 in accordance with embodiments. For illustrative purposes, volumetric information 800 is representative of a slice/layer near the "top" of the imaged breast, but the invention is not so limited. Due to the curved surface, the anatomy present at this height has a small "footprint" (illustrated by shaded area 830). For convenience of interpretation and to provide anatomical context, the "maximum footprint" of the breast (from other slices) is shown in the image, e.g., in form of a superimposed outline 820. In some implementations, other additional information providing anatomical context (or similar information) may be used as well.

In accordance with embodiments, a volumetric reconstruction having non-uniform voxels and/or non-planar slices (perhaps of variable thickness) corresponding to an exact model of the breast can be displayed. These non-uniform voxels can be at least partially aligned with anatomical features of the patient for reference (e.g., a slice "parallel" to the patient's skin line). In one implementation, displayed slices can be aligned with anatomical features (e.g., the skin line), and the displayed slices (starting from either top or bottom) are displaying the anatomical features from the skin line "inwards". This approach can also be used as reformatting of data that was reconstructed on Cartesian grid.

Figure 4A:
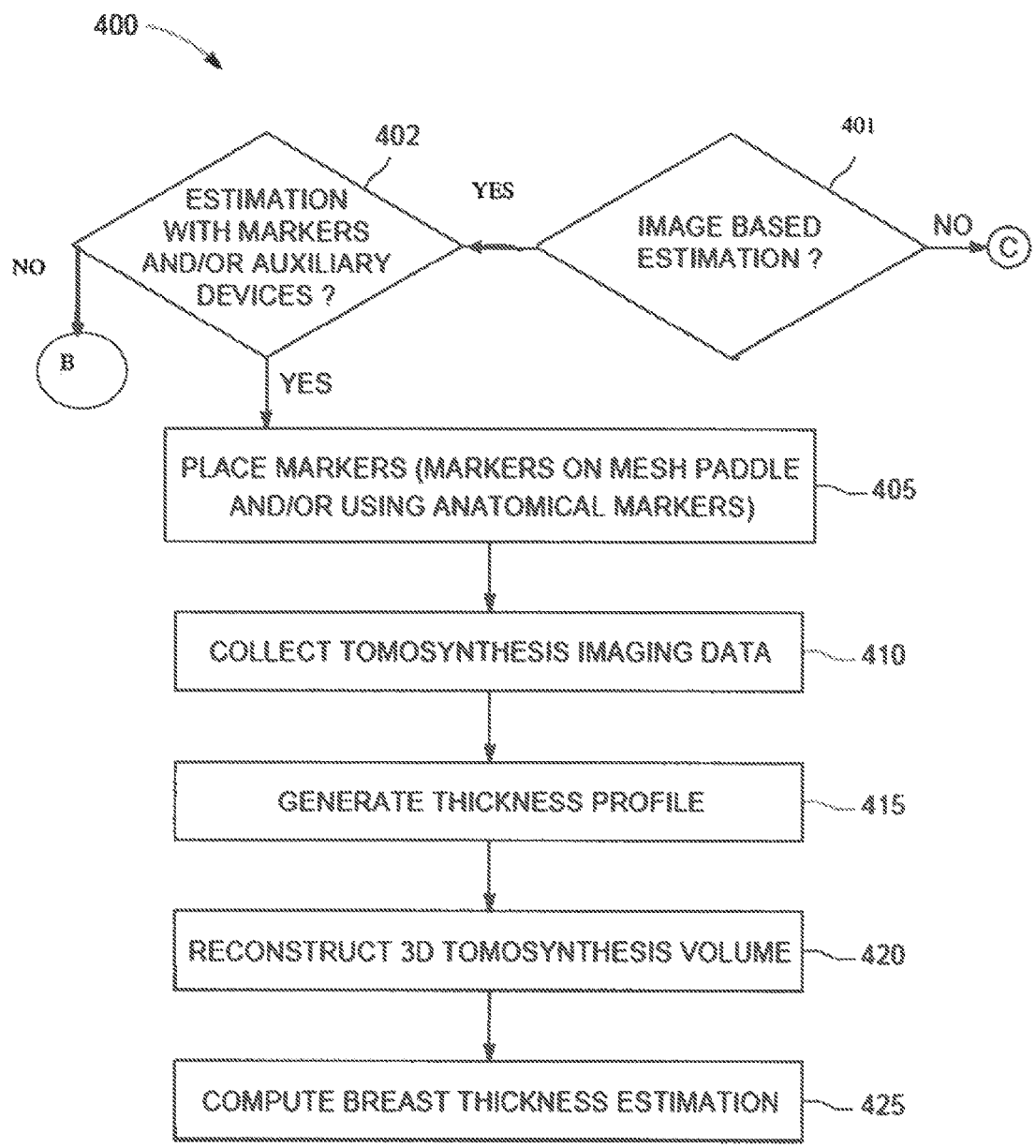
FIGS. 4A-4C depict a process for breast thickness estimation in accordance with embodiments.
Figure 4B:
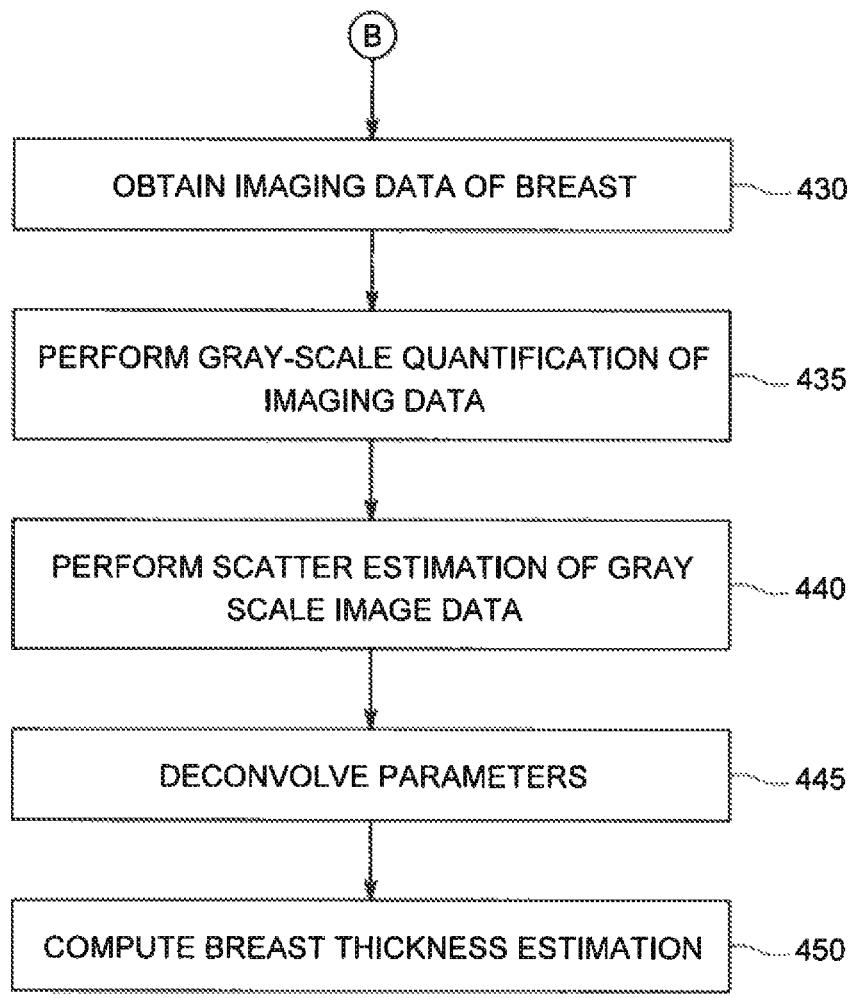
Figure 4C:
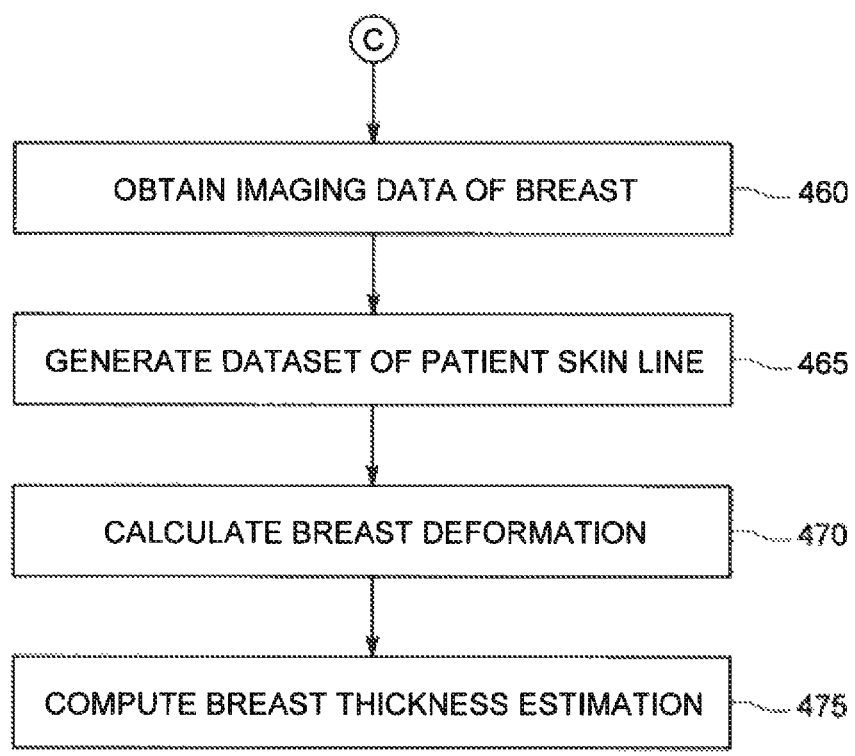

FIGS. 4A-4C depict process 400 for breast thickness estimation (FIG. 3, step 310) in accordance with embodiments. A determination is made, step 401, as to whether the breast thickness estimation is to be an image based estimation or a model based estimation (process 400 continues on FIG. 4C). At step 402, a determination is made as to whether the image based estimation is to be made with markers and/or auxiliary devices (process 400 continues on FIG. 4A), or is to be an intensity based estimation (process 400 continues on FIG. 4B).

If the estimation is made with markers, the markers are placed (step 405) on the flexible paddle, on the patient's skin, or both. These markers can be wires, fibers, metal pellets (ball bearings, a/k/a BBs) or other shapes/materials. If ultrasound coupling pads, stand-offs or gel filled bags etc. are used to perform the ultrasound coupling for the imaging scan, small particles of metal, plastic, graphite, etc. can be embedded in the gel to be used for calibration. The markers attenuate the X-ray, and the marker's position in the volume may be determined from the image data (e.g., by an initial reconstruction step, followed by identifying the position of the markers in the reconstructed volume; or by alternative methods). The position of the markers may be used to delineate the boundary between the patient's skin and the flexible compression paddle, and/or the height of the imaged breast. In addition to, or instead of additional markers, anatomical markers may be used. These anatomical markers may include the patient's skin texture, cooper's ligaments, lymph node, etc. (which can generally be identified in reconstructed volumetric datasets in tomosynthesis, thereby determining the "top layer" of the imaged breast and thus the associated thickness profile). These methods to determine the thickness profile may be used in conjunction with appropriate smoothness constraints (e.g., height is a smooth function of x/y).

For marker-based approaches, tomosynthesis imaging data is collected, step 410, so that a thickness profile can be generated. This thickness profile can then feed into the reconstruction of the 3D tomosynthesis volume, step 420, from the same projections. If using auxiliary devices (next paragraph), the X-ray projection images are not required for determining the thickness profile.

In alternative embodiments, auxiliary devices may be used to measure/determine the thickness profile of the imaged breast. For example, a computer vision system may be utilized, where the height may be estimated by using multiple cameras and visible structures in the compression paddle, or by using a single camera in conjunction with gridlines (or similar patterns) that are projected onto the breast/the compression paddle (and which can be used to determine the thickness profile from the deformation of the projected grid in the visible images captured with the camera).

The camera does not need to operate in the visible spectrum and can operate in the near IR or UV spectrum, for example to protect patient privacy. Other alternative sensors and approaches such as electromagnetic sensors, gyroscopes, magnetoresistance, inertial, magnetic etc. may be used as well to determine the breast thickness profile. In some implementations, the thickness profile can be obtained from the readout of the mechanical scanning profile of the ultrasound probe, when an ultrasound scan is performed in conjunction with the tomosynthesis scan (i.e., the thickness profile is determined as a function of the varying height of the ultrasound probe as a function of x/y position). In yet other embodiments, the thickness profile may be extracted from the ultrasound image data, where the location of the bottom plate/detector cover may be visible and determined. The "depth" of the bottom plate in the ultrasound data may then serve as an estimate of the local thickness of the breast (at the current location of the ultrasound probe). In some implementations, this estimate can include a correction term that accounts for the breast deformation due to the pressure of the ultrasound probe on the breast.

If the mechanical scanning profile of the ultrasound probe is constrained to be in a plane (e.g., no vertical motion), the thickness profile can be obtained from the nominal shape of the compression paddle, where the mesh paddle is taut enough to make the breast shape conform. By way of example, the flexible paddle depicted in FIGS. 5A-5B has a curved front frame holding the mesh.

If the mechanical scanning profile of the ultrasound probe is not constrained to a plane and the probe is allowed to further compress the breast during scanning, the height of the breast as measured in the ultrasound imaging will be smaller than for the X-ray imaging. The vertical motion of the ultrasound probe can be measured and recorded when the ultrasound imaging is performed. The vertical motion of the probe relative to the compression paddle height can be leveraged with the ultrasound imaging to build a 3D model of the breast during the X-ray imaging. The height variation of the ultrasound probe during the scanning motion in addition to the height of determined from the ultrasound imaging can be used to compute, step 425, an estimation of the breast thickness.

FIG. 4B depicts an image intensity-based process for breast thickness estimation in accordance with embodiments. At step 430, imaging data of the breast is obtained (FIG. 3, step 305). A gray scale quantification of the imaging data is performed, step 435. The gray scale values in the projection images correspond essentially to the sum of the primary beam (i.e., non-scattered radiation) and scattered radiation. In order to estimate the thickness of the imaged breast from the image directly, the image content corresponding to scattered radiation must be estimated.

A scatter estimation is performed, step 440, on the gray scale image data. In one embodiment a small number of beam blocks (e.g., small circular BBs consisting of lead or steel) may be used to estimate scatter. Since these beam blocks block the primary radiation, the observed signal "behind" these beam blocks correspond to scatter only. If placed judiciously (e.g., at some small distance above the compression paddle, or with some appropriate displacement between views), in each region covered by beam block, it might be that data corresponding to only a single tomosynthesis view is lost—i.e., the loss's impact on image quality is minimal.

Scatter may also be estimated from observed pixel values in the projection views "just outside" of the region covered by the imaged anatomy. These values indicate the amount of scatter near the skin line of the imaged breast, and can be used to estimate the scatter distribution across the full breast. The scatter profile can be estimated by interpolating within each view and between views using information on how adjacent scatter maps resemble each other across view angles.

At step 445, the breast thickness can be deconvolved from the parameters of scatter plus monotonic gray scale images. This deconvolution can be a function of different parameters, for example, varying breast thickness, breast composition/density, etc. The breast thickness can be estimated, step 450, by backing out the scatter estimation (via predicted primary, based on path length).

FIG. 4C depicts a model-based process for breast thickness estimation in accordance with embodiments. At step 460, imaging data of the breast is obtained (FIG. 3, step 305). A dataset is generated, step 465, containing nominal compressed breast thickness data (e.g., a measured height of the compression paddle), a skin line profile (i.e., the location of the 2D skin line in the collected projection views), and compression force data. In some implementations position and shape of an about vertical skin line (e.g., reconstructed from the 2D skin line extracted from the projection images) can be added to the dataset to further model the patient's breast. In one embodiment, the modeling of the breast thickness utilizes just the curvature of the compression paddle (to define the curvature of the breast thickness profile) and height reported by the system at the calibration point (as a constant offset) to define the thickness profile.

Using the compression force and dataset information on the patient's breast, the deformation of the breast can be calculated, step 470. In some implementations, the model can be more involved containing finite-element modeling. The breast deformation calculation applies the mechanical properties of the breast tissue with the compression force applied by the mesh paddle. The breast thickness can be calculated/estimated, step 475, by taking into account the model-based breast deformation obtained at step 470. In some implementations, hybrid methods (i.e., methods combining aspects of two or more of the different methods discussed above) for determining the breast thickness profile may be used as well.

Breast density may be estimated from one or more individual projection images, or the volumetric reconstruction, or a combination thereof. Detailed knowledge of the breast thickness profile can contribute to the breast density estimation. Once the breast thickness is estimated, the volumetric breast density can be computed, step 325. The breast density can be computed using the breast thickness map applied to a physics, model-based, density estimation method. In other implementations, a differential processing method can be used to get a density difference map comparing to a complete fatty breast. Alternatively, prior information (e.g., using prior knowledge of a 100% fat tissue composition near the skin line, etc.), surface geometry, or other breast thickness or density related information from an ultrasound image can be used to estimate the total volume or percentage of dense tissue in the breast. If a volumetric reconstruction is used for the density estimation calculation this reconstruction may be a separate reconstruction performed to preserve the correct voxel density values rather than radiologist image quality. For example, smoothness constraints on the skin-line are not necessarily maintained.

In accordance with some embodiments, a computer program application stored in non-volatile memory or computer-readable medium (e.g., register memory, processor cache, RAM, ROM, hard drive, flash memory, CD ROM, magnetic media, etc.) may include code or executable instructions that when executed may instruct and/or cause a controller or processor to perform methods discussed herein such as a method for extracting compressed breast thickness profile to improve breast density estimation and image reconstruction when using a flexible mesh paddle, as described above.

The computer-readable medium may be a non-transitory computer-readable media including all forms and types of memory and all computer-readable media except for a transitory, propagating signal. In one implementation, the non-volatile memory or computer-readable medium may be external memory.

Although specific hardware and methods have been described herein, note that any number of other configurations may be provided in accordance with embodiments of the invention. Thus, while there have been shown, described, and pointed out fundamental novel features of the invention, it will be understood that various omissions, substitutions, and changes in the form and details of the illustrated embodiments, and in their operation, may be made by those skilled in the art without departing from the spirit and scope of the invention. Substitutions of elements from one embodiment to another are also fully intended and contemplated. The invention is defined solely with regard to the claims appended hereto, and equivalents of the recitations therein.

What is claimed is:

1. A mammography imaging system, comprising:
   an X-ray source;
   an X-ray detector spaced apart from the X-ray source; and
   an image data acquisition system for acquiring mammography image data; and
   compression assembly positioned between the X-ray source and the X-ray detector, the compression assembly including a movable flexible compression paddle and a support plate spaced apart from each other and configured to hold an object to be imaged therebetween, and wherein the movable flexible compression paddle is formed of a flexible film material or flexible mesh material held by a frame, and wherein the flexible film or flexible mesh material conforms to the shape and size of the object to be imaged.

2. The mammography imaging system of claim 1, wherein the X-ray source is movable in a one, two, or three dimensional trajectory relative to the object to be imaged.

3. The mammography imaging system of claim 1, wherein the X-ray detector is stationary.

4. The mammography imaging system of claim 1, wherein the X-ray detector is configured to move either independently or in synchrony with the X-ray source.

5. The mammography imaging system of claim 1, wherein the X-ray detector is disposed beneath the support plate of the compression assembly.

6. The mammography imaging system of claim 1, wherein the compression assembly is configured to compress the object to be imaged during a mammography image acquisition.

7. The mammography imaging system of claim 1, wherein the support plate is a flat plate on which the object to be imaged may rest and the movable flexible compression paddle lowers onto the object to be imaged to effect compression.

8. The mammography imaging system of claim 1, wherein the movable flexible compression paddle includes markers.

9. The mammography imaging system of claim 1, wherein the movable flexible compression paddle is radiolucent and sonolucent.

10. The mammography imaging system of claim 1, wherein the support plate is radiolucent and sonolucent.

11. A tomography imaging system, comprising:
    an X-ray source;
    an X-ray detector spaced apart from the X-ray source; and
    an image data acquisition system for acquiring tomography image data; and
    a compression assembly positioned between the X-ray source and the X-ray detector, the compression assembly including a movable flexible compression paddle and a support plate spaced apart from each other and configured to hold an object to be imaged therebetween, and wherein the movable flexible compression paddle is formed of a flexible film material or flexible mesh material held by a frame, and wherein the flexible film or flexible mesh material conforms to the shape and size of the object to be imaged.

12. The tomography imaging system of claim 11, wherein the X-ray source is movable in a one, two, or three dimensional trajectory relative to the object to be imaged.

13. The tomography imaging system of claim 11, wherein the X-ray detector is stationary.

14. The tomography imaging system of claim 11, wherein the X-ray detector is configured to move either independently or in synchrony with the X-ray source.

15. The tomography imaging system of claim 11, wherein the X-ray detector is disposed beneath the support plate of the compression assembly.

16. The tomography imaging system of claim 11, wherein the compression assembly is configured to compress the object to be imaged during a mammography image acquisition.

17. The tomography imaging system of claim 11, wherein the support plate is a flat plate on which the object to be imaged may rest and the movable flexible compression paddle lowers onto the object to be imaged to effect compression.

18. The tomography imaging system of claim 11, wherein the movable flexible compression paddle includes markers.

19. The tomography imaging system of claim 11, wherein the movable flexible compression paddle is radiolucent and sonolucent.

20. The tomography imaging system of claim 11, wherein the support plate is radiolucent and sonolucent.

21. A multi-modality imaging system, comprising:
    X-ray imaging subsystem including:
    an X-ray source;
    an X-ray detector;
    an X-ray image data acquisition system for acquiring X-ray image data;
    a compression assembly positioned between the X-ray source and the X-ray detector, the compression assembly including a movable flexible compression paddle and a support plate spaced apart from each other and configured to hold an object to be imaged therebetween;
    an ultrasound imaging subsystem including:
    an ultrasound probe; and
    an ultrasound data acquisition and image processing module.

22. The multi-modality imaging system of claim 21, wherein the ultrasound probe is used for transmitting a plurality of ultrasound signals into the object to be imaged and for receiving a plurality of reflected ultrasound signals from the object to be imaged.

23. The multi-modality imaging system of claim 22, wherein the plurality of reflected ultrasound signals from the object to be imaged include information about thickness, size, and location of various tissues, organs, tumors, and anatomical structures in relation to the plurality of transmitted ultrasound signals.

24. The multi-modality imaging system of claim 22, wherein the plurality of reflected ultrasound signals received by the ultrasound probe are processed for constructing a volumetric image of the object to be imaged.

25. The multi-modality imaging system of claim 21, wherein the ultrasound imaging subsystem employs beam steering techniques to help image all areas of the object to be imaged.

26. The multi-modality imaging system of claim 21, wherein movement and operation of the ultrasound probe is automated.

27. The multi-modality imaging system of claim 21, wherein the ultrasound probe is automatically brought into contact with the object to be imaged or with the movable flexible compression paddle compressing the object to be imaged.

28. The multi-modality imaging system of claim 21, wherein the ultrasound data acquisition and image processing module sends signals to and receives signals from the ultrasound probe during an ultrasound imaging procedure.

29. The multi-modality imaging system of claim 21, wherein the compression assembly is configured to compress the object to be imaged during both tomosynthesis and ultrasound image acquisitions.

30. The multi-modality imaging system of claim 21, wherein the compression assembly includes a hybrid compression paddle that includes a removable rigid plate and a flexible compression mesh component, wherein the removable rigid plate may be removed for an ultrasound image acquisition, leaving only the flexible compression mesh component in contact with the object to be imaged.

* * * * *